US008512648B2

(12) United States Patent
Bau-Madsen

(10) Patent No.: US 8,512,648 B2
(45) Date of Patent: Aug. 20, 2013

(54) MICROFLUIDIC DEVICE

(75) Inventor: Niels Kristian Bau-Madsen, Hellerup (DK)

(73) Assignee: Scandinavian Micro Biodevices APS, Farum (DK)

( * ) Notice: Subject to any disclaimer, the term of this patent is extended or adjusted under 35 U.S.C. 154(b) by 0 days.

(21) Appl. No.: 13/056,420

(22) PCT Filed: Jul. 29, 2009

(86) PCT No.: PCT/DK2009/050191
§ 371 (c)(1), (2), (4) Date: Jan. 28, 2011

(87) PCT Pub. No.: WO2010/012281
PCT Pub. Date: Feb. 4, 2010

(65) Prior Publication Data

US 2011/0143383 A1 Jun. 16, 2011

Related U.S. Application Data

(60) Provisional application No. 61/084,516, filed on Jul. 29, 2008.

(30) Foreign Application Priority Data

Jul. 29, 2008 (DK) ................................ 2008 01047

(51) Int. Cl.
*G01N 15/06* (2006.01)
*G01N 33/00* (2006.01)
*G01N 33/48* (2006.01)

(52) U.S. Cl.
USPC ............ 422/503; 422/50; 422/68.1; 422/502; 422/504; 422/505

(58) Field of Classification Search
USPC .................. 422/50, 68.1, 502, 504, 505, 503
See application file for complete search history.

(56) References Cited

U.S. PATENT DOCUMENTS 5,569,608 A 10/1996 Sommer (Continued)

FOREIGN PATENT DOCUMENTS

WO WO 99/64840 A1 12/1999
WO WO 2004/042402 A2 5/2004

(Continued)

OTHER PUBLICATIONS

Search Report dated Sep. 11, 2009, issued by the Nordic Patent Institute in corresponding International Patent Application No. PCT/DK2009/050191.

*Primary Examiner* — Brian J Sines
(74) *Attorney, Agent, or Firm* — Buchanan Ingersoll & Rooney PC

(57) ABSTRACT

A microfluidic device comprising a flow channel with an inlet and a gas escape opening is described. The flow channel comprises a liquid flow channel section and a flow controlling section downstream to the liquid flow channel section and upstream to or coinciding with the gas escape opening. The flow controlling section provides a flow resistance to gas, which is sufficiently high to reduce velocity of a capillary flow of a liquid in the liquid flow channel section.
The microfluidic device with the flow controlling section provides a device in which the velocity of the flow can be reduced to a desired level.
Also is described a method of performing a test using the microfluidic device.

19 Claims, 10 Drawing Sheets

(56) References Cited

U.S. PATENT DOCUMENTS

| | | | |
|---|---|---|---|
| 6,575,188 | B2 | 6/2003 | Parunak |
| 6,591,852 | B1 | 7/2003 | McNeely et al. |
| 6,637,463 | B1 | 10/2003 | Lei et al. |
| 2003/0103878 | A1 | 6/2003 | Morse et al. |
| 2003/0196714 | A1 | 10/2003 | Gilbert et al. |
| 2004/0011975 | A1 | 1/2004 | Nicoli et al. |
| 2004/0206408 | A1 | 10/2004 | Peters et al. |
| 2004/0216790 | A1 | 11/2004 | Chen et al. |
| 2005/0020666 | A1 | 1/2005 | Mukherjee et al. |
| 2009/0050542 | A1 * | 2/2009 | Leary et al. .................. 209/589 |

FOREIGN PATENT DOCUMENTS

| | | | |
|---|---|---|---|
| WO | WO 2006/009724 | A2 | 1/2006 |
| WO | WO 2006/098752 | A2 | 9/2006 |

* cited by examiner

MICROFLUIDIC DEVICE

TECHNICAL FIELD

The invention relates to a microfluidic device comprising a flow channel for a liquid flow. The device of this type may for example be for use in test of a biological fluid sample, such as blood, urine saliva or other.

BACKGROUND ART

Microfluidic devices comprising a microfluidic structure, such as a flow channel are well known. Such microfluidic devices are often used for performing tests of fluidic samples, such as of biological fluids e.g. for performing blood tests, such a coagulation tests e.g. for determining the coagulation rate in a blood sample or agglutination tests e.g. for determining blood type of a blood sample.

In particular such microfluidic devices are used for performing tests on biological liquids.

Such devices normally depend totally or partly on capillary forces to drive a liquid into a channel of the device. Alternatively or additionally external forces may be applied to drive a liquid in the channel(s). The geometry of the channels is often very important. External forces which may be applied to fill the flow channel(s) may for example be centrifugal forces, pumping forces and similar.

Microfluidic devices of this kind are used for performing test of liquid samples. Often it is desired to subject the liquid to various treatments in the microfluidic device, e.g. mixing with other components, dissolving a reagent and optionally allowing the liquid sample to react with a reagent. It is therefore normally desired that the microfluidic device comprises some means for controlling the flow of the liquid sample along the flow path.

U.S. Pat. No. 6,575,188 discloses a microfluidic device comprising a temperature controlled valve. The microfluidic device comprises a thermally responsive substance in its passage which substance can obstruct and open the passage in relation to actuation of a heat source.

US 2003/0196714 discloses a microfluidic device including a bubble valve for regulating a fluid flow through a micro channel. The bubble valve includes a fluid meniscus interfacing the micro channel interior and an actuator for deflecting the membrane into the micro channel interior to regulate the fluid flow. The actuator generates a gas bubble in a liquid in the micro channel when a sufficient pressure is generated on the membrane.

US 2004/0206408 discloses a microfluidic device with a switch for stopping a liquid flow during a time interval. The microfluidic device comprises a capillary stop e.g. provided by a sudden change of the geometrical properties. Similar devices with capillary stops are e.g. disclosed in U.S. Pat. Nos. 6,637,463 and 6,591,852.

U.S. Pat. No. 5,230,866 discloses a microfluidic device with a capillary stop-flow junction comprising means for trapping a gas in the capillary passageway to establish a back-pressure to stop the flow in said passageway. When this means for trapping a gas is removed, the gas can continue to flow.

THE INVENTION AND EMBODIMENTS THEREOF

The object of the invention is to provide a novel microfluidic device of the type which comprises a channel for a liquid fluid, wherein a desired velocity of a liquid flow in the channel can be obtained.

Accordingly a novel microfluidic device has been provided. The microfluidic device of the invention and embodiments thereof are defined in the claims and/or described in the description.

The microfluidic device comprises a flow channel with an inlet and a gas escape opening. The flow channel comprises a liquid flow channel section and a flow controlling section downstream to the liquid flow channel section and upstream to or coinciding with the gas escape opening. The flow controlling section provides a flow resistance to gas, which is sufficiently high to reduce velocity of a capillary flow of a liquid in the liquid flow channel section for example compared to what it would have been without the gas flow resistance of the flow controlling section.

A liquid flow in a microfluidic device without a flow controlling section is highly dependent on the viscosity of the liquid, the capillary effect, the wettability of the inner walls of the flow channel and optional external forces. As described above, previous microfluidic devices which can completely stop a flow have been provided. By the present invention the velocity of the liquid flow can be arranged as desired, by using a whole new principle wherein resistance of escaping gas is used as a regulating factor.

By the microfluidic device it has also shown that it is possible to obtain a very stable liquid velocity.

According to the invention the flow controlling section provides that the flow resistance to gas increases the flow resistance to the liquid in the liquid flow channel thereby making it much simpler to control the flow and the flow velocity of the liquid in the liquid flow channel.

According to a theory it is believed that when fluids flow they have a certain amount of internal friction called viscosity. It exists in both liquids and gases and is essentially a friction force between different layers of fluid as they move past one another. In liquids the viscosity is due to the cohesive forces between the molecules whilst in gases the viscosity is due to collisions between the molecules. The viscosity of a liquid sample therefore has an influence on the flow velocity of the said liquid sample.

Furthermore according to this theory, when a fluid (liquid or gas) flows past a stationary wall e.g. as in a channel of a microfluidic device, the fluid right close to the wall does not move. However, away from the wall the flow speed is not zero. Therefore, the molecules at the surface of the stationary wall are essentially at rest and the velocity of the flow will—without other regulating forces—vary with distance from the stationary wall.

According to one embodiment of the invention, the microfluidic device provides a relatively high fluid driving force—e.g. capillary force and provides a flow resistance which limits the flow by the flow controlling section. Thereby the above effects will be less pronounced, i.e. the difference between the movements of the liquid over the cross section of the flow channel can be reduced. And a more flat flow front can be obtained.

The microfluidic device of the invention comprises at least one inlet for introducing a liquid sample into the liquid flow channel. The inlet may be of any type and shape e.g. as known from prior art microfluidic devices. The microfluidic device of the invention comprises at least one flow channel, such as two or more. The flow channel can have any shape e.g. with a cross sectional shape selected from round, ellipsoidal, semi ellipsoidal, quadrilateral polygonal, square, rectangular and trapezoidal shapes, where any edges optionally being rounded. The shape of the flow channel will often be designed in accordance with the desired use of the microfluidic device. Examples of flow channels and shapes are described below. In one embodiment the microfluidic device comprises two or more distinct liquid channel sections.

The microfluidic device of the invention comprises at least one gas escape opening for allowing gas to escape from the channel. The gas escape opening may be of any type and shape e.g. as known from prior art microfluidic devices. The gas escape opening may for example be arranged to allow gas to escape completely out of the microfluidic device or it may allow the gas to escape into a gas collecting chamber e.g. in the form of an inflatable unit.

The microfluidic device of the invention comprises at least one liquid flow channel section. The liquid flow channel section may in principle have any shape and length provided that at least one section thereof can provide a capillary driven flow of a liquid, such as an aqueous liquid and/or blood. In one embodiment the liquid flow channel section comprises one or more chambers, e.g. a reaction chamber where the liquid is allowed to react with, dissolve and/or disperse a component applied in the chamber; a mixing chamber for mixing the liquid with one or more other liquids or a measuring chamber where one or more properties of the liquid can be measured and/or determined. In general it is desired that the liquid flow channel section has at least one dimension (often the width dimension) of at least about 100 μm, such as at least 500 μm. The other dimension(s) (e.g. the depth if the channel has an essentially rectangular cross-section), may be smaller e.g. down to about 25 μm if desired.

In this context a chamber means a subsection of the channel (here the liquid flow channel section) which has a larger cross-sectional area than the average cross-sectional area of the channel section in question, such as a cross sectional area which is at least 25%, such as at least 50%, larger than the average cross sectional area of the channel section in question. The chamber may for example have a larger cross sectional area than the average cross sectional area of the channel in question by being wider. The depth of the channel including the chamber may be substantially constant or it may vary.

According to the invention the microfluidic device comprises a flow controlling section which provides a flow resistance to gas, which is sufficiently high to reduce velocity of a capillary flow of a liquid in the liquid flow channel section.

In one embodiment the flow controlling section provides a flow resistance to gas, which is sufficiently high to reduce velocity of a capillary flow of a liquid in the liquid flow channel section compared to what the velocity would have been without the flow controlling section.

The flow controlling section preferably is arranged to provide a gas resistance which is essentially constant during filling of at least a major part of the liquid flow channel. The flow controlling section may in principle have any shape provided that it results in a gas resistance when gas is driven away by the liquid due to filling of the liquid flow channel with the liquid, which gas resistance has a significant influence on the flow velocity of the liquid flowing in the liquid flow channel.

In one embodiment the flow controlling section is in the form of at least one narrow passage in the flow channel. The one or more narrow passage may be placed anywhere downstream to the liquid flow channel section and upstream to or coinciding with the gas escape opening, A narrow passage should herein be understood to be a passage in the flow controlling section for gas where gas can pass and progress towards or out of the escape opening. The one or more narrow passages should be sufficiently narrow to provide the desired gas resistance.

In embodiments where the flow controlling section comprises two or more narrow passages, the two or more narrow passages may be placed in the flow controlling section totally or partly side by side and/or totally or partly after each other along the length of the flow controlling section. The length of the flow controlling section is determined to be the length along the flow of the gas. The two or more narrow passages may be essentially identical or they may differ from each other e.g. in size and/or shape.

In one embodiment the flow controlling section comprises a narrow passage coinciding with the gas escape opening.

In one embodiment the flow controlling section is in the form of a plurality of narrow passages in the flow channel. The plurality of narrow passages may for example be provided by a gas permeable membrane placed in the flow channel or placed coinciding with the gas escape opening. As an example of a gas permeable membrane which can be used can be mentioned porous and non porous membranes such as a PTFE membrane (e.g. Gore-Tex) and track etched membranes e.g. of polyester and/or polycarbonate, such as the track etched polycarbonate membranes sold under the trade name Isopore, by Sigma-Aldrich Danmark A/S.

The gas permeable membrane may in one embodiment be placed as a tape to cover the channel leading to the escape opening.

In one embodiment the gas permeable membrane is in the form of a filter material arranged in the channel leading to the escape opening.

In one embodiment where the flow controlling section comprises one or more narrow passages, the total cross sectional area of the one or more narrow passages is about 5% or less, such as about 2% or less, such as about 1% or less, such than about 0.1% or less than the smallest cross sectional area of the liquid flow channel section. In general the longer the length of narrow passage the larger the total cross sectional area can be. The skilled person will be able to determine the desired total cross sectional area for a given microfluidic device design within the scope of the invention.

In one embodiment where the flow controlling section comprises one or more narrow passages, the total cross sectional area of the one or more narrow passages is about 10,000 $\mu m^2$ or less, such as about 1000 $\mu m^2$ or less, such as about 100 $\mu m^2$ or less.

In one embodiment the flow controlling section is in the form of a flow controlling channel section, said flow controlling channel section has a length and a cross sections profile along its length arranged to provide a channel flow resistance which is sufficiently high to reduce velocity of a capillary flow of a liquid in the liquid flow channel section.

The flow controlling channel section may have any length and any cross sections profile along its length as long as it provides the desired gas resistance. For simplification in production it is in one embodiment preferred that the flow controlling channel section has an essentially constant cross sectional shape along its length.

The length of the flow controlling channel section may be determined from a flow controlling channel section entrance to the gas escape opening, where the flow controlling channel section entrance is the point along the flow channel from its inlet and towards its gas escape opening where a liquid flow driven exclusively by capillary forces will terminate flow.

In one embodiment the flow controlling channel section is arranged such that the liquid sample e.g. the biological sample cannot flow into the flow controlling channel section by capillary forces. This is normally referred to as a “liquid flow stop”. The liquid flow stop may e.g. be provided by arranging the walls of the flow controlling channel section with a relatively low surface energy (hydrophobic liquid flow stop) or otherwise reduce any generation of capillary forces in the flow controlling channel section and/or providing at least a part—preferably adjacent to the liquid flow channel—of the flow controlling channel section with sufficiently small cross sectional area whereby a liquid flow resistance will prevent the entrance of the liquid into the flow controlling channel section. The simplest way to provide a liquid flow stop is normally to use a hydrophobic liquid flow stop, or a geometric liquid flow stop. A geometric flow stop is provided by arranging an abrupt increase in cross section so that an edge, such as an edge of at least about 60 degrees, preferably at least about 80 degrees is provided. The geometric liquid flow stop and the hydrophobic liquid flow stop can be relatively short, e.g. about 2 mm in length or more, such as about 5 mm in length or more.

In one embodiment the length of the flow controlling channel section is determined from a flow controlling channel section entrance to the gas escape opening, where the flow controlling channel section entrance is the point along the flow channel from its inlet and towards its gas escape opening where the cross sectional area is reduced to about 10,000 $\mu m^2$ or less, such as about 1000 $\mu m^2$ or less, such as about 100 $\mu m^2$ or less.

In one embodiment the length of the flow controlling channel section is determined from a flow controlling channel section entrance to the gas escape opening, where the flow controlling channel section entrance is the point along the flow channel from its inlet and towards its gas escape opening where the cross sectional area of the channel is gradually or abruptly reduced with at least about 95%, such as at least about 99%. If desired a liquid flow stop, such as a hydrophobic liquid flow stop or a geometric liquid flow stop may be arranged prior to or in the flow controlling section.

In one embodiment the cross section of the flow controlling channel section along its length varies. The flow controlling channel section may for example comprise one or more low cross-section part (narrow passage) and one or more high cross-section parts where the low cross-section parts has a cross-section which is significantly smaller than the cross section of the high cross-section parts, such as at least about 25% smaller, such as at least about 50% smaller, such as at least about 90% smaller than the high cross-section parts. In situations where the flow controlling channel section comprises such varying cross section along its length, the flow of gas through the flow controlling channel section may be increasingly turbulent.

In order to obtain a very stable and reproducible gas resistance by the flow controlling channel section the flow controlling channel section should have a substantially length. Experiments have shown that a flow controlling channel section having a length of at least about 10 cm, such as at least about 25 cm is beneficial to the gas resistance stability and the reproducibility of the microfluidic device. Longer length may show to be in even more stable with respect to gas resistance.

In one embodiment the flow controlling channel section has a length which is at least 2, times, such as at least 5 times, such as at least 10 times or even 20 times or more longer than the liquid flow channel section.

In one embodiment the cross sectional area in at least a length of the flow controlling channel section is about 10,000 $\mu m^2$ or less, such as about 1000 $\mu m^2$ or less, such as about 100 $\mu m^2$ or less.

In one embodiment the cross sectional area is at least about 10%, such as at least about 25%, such as at least about 50%, such as at least about 75%, such as about 100% of the length of the flow controlling channel section is about 10,000 $\mu m^2$ or less, such as about 1000 $\mu m^2$ or less, such as about 100 $\mu m^2$ or less.

In one embodiment the average cross sectional area along the length of the flow controlling channel section is about 10,000 $\mu m^2$ or less, such as about 1000 $\mu m^2$ or less, such as about 100 $\mu m^2$ or less.

In one embodiment the average cross sectional area along the length of the flow controlling channel section is at least about 90%, such as at least about 95%, such as at least about 99%, such as at least about 99.9 smaller than the average cross sectional area of the liquid flow channel section.

The flow controlling section provides a flow resistance (gas flow resistance) which is sufficiently high to reduce velocity of a capillary flow of a liquid in the liquid flow channel. Preferably the gas flow resistance should provide a significant reduction of the velocity of a capillary flow of a liquid in the liquid flow channel section compared to what it would have been without the flow controlling section.

The liquid may be water or any undiluted or diluted biological liquid or combinations or fractions thereof. More preferably the liquid may be selected from water, blood, plasma, saliva, urine combinations and fractions thereof. For test purpose it is desired that the liquid used should be selected from water, blood, plasma, saliva or urine.

In other words it is desired that the flow controlling section provides a flow resistance (gas flow resistance) which is sufficiently high to reduce velocity of a capillary flow of a liquid in the liquid flow channel, when the liquid is selected from water, blood, plasma, saliva or urine.

Unless other is mentioned all tests and properties described herein are determined at standard conditions (1 atmosphere, 20° C.).

In one embodiment the flow controlling section provides a flow resistance which is sufficiently high to reduce velocity of a capillary flow of a liquid in the liquid flow channel section with at least about 10%, such as at least about 25%, such as at least about 50%, such as at least about 75%, such as at least about 90%, such as at least about 99% compared to what the velocity would have been without said flow controlling channel section.

In one embodiment the flow controlling channel section has a length and a cross section profile along its length arranged to provide a channel flow resistance which is sufficiently high to reduce velocity of a capillary flow of a liquid in the liquid flow channel section with at least about 10%, such as at least about 25%, such as at least about 50%, such as at least about 75%, such as at least about 90%, such as at least about 99% compared to what the velocity would have been without said flow controlling channel section.

In one embodiment the flow controlling section in the form of a flow controlling channel section and comprising a length and cross-sectional dimension or comprising at least one narrow passage, provides a flow resistance against gas which is sufficiently high to significantly affect a liquid fluid flow in the liquid flow channel where the liquid is blood, plasma or a fraction of blood undiluted or diluted form.

In one embodiment the flow controlling section provides a flow resistance against gas which is higher that the flow resistance of a liquid fluid flow in the liquid flow channel.

In one embodiment the flow resistance against gas in the flow controlling section is so high that a liquid flow velocity in the liquid flow channel section is essentially not reduced by liquid flow resistance in said liquid flow channel section.

In one embodiment the flow controlling section provides a flow resistance against gas which is sufficiently high to be the controlling factor of the velocity of a liquid fluid flow in the liquid flow channel.

As the liquid flows into the liquid flow channel it will seek to drive away the gas therein. The gas will flow toward the escape opening but the flow will be limited by the gas resistance. A balance will be reached where the gas flow out of the flow controlling section is essentially constant and where the gas pressure within the not yet filled liquid flow channel is essentially constant and above atmosphere pressure.

In one embodiment where a balance will be reached where the gas flow out of the flow controlling section is essentially constant and where the gas pressure within the not yet filled liquid flow channel is essentially constant, it is desired that the gas pressure within the not yet filled liquid flow channel is at least about 110 kPa, such as at least about 115 kPa, such as at least about 125 kPa.

In one embodiment the liquid flow is a flow of a liquid under conditions where the liquid has a viscosity of from about 0.1 to about 10 mPaS, such as from about 1 to about 7 mPaS, such as from about 1.5 to about 5 mPaS.

The gas may in principle be any gas which does not react with the liquid, such as any inert gas, such as oxygen, nitrogen, carbon oxides and air. Normally the gas will be air.

The flow controlling channel section may be straight or it may be bended. In situations where the flow controlling channel section is relatively long, such as about 5 cm or longer it is desired that the flow controlling channel section is bended, preferably the flow controlling channel is coiled or meander shaped.

When providing the flow controlling channel section in bended form, care should be taken that the gas cannot make short cuts. This feature of an embodiment of the invention is described and explained further with reference to a specific example in the description of the drawings.

In one embodiment the microfluidic device comprises at least one gas escape opening in the form of an opening into an inflatable unit of the device.

In one embodiment the microfluidic device comprises at least one gas escape opening in the form of an opening for gas, preferably air to escape out of the device.

In one embodiment the microfluidic device comprises two or more gas escape openings, preferably at least one of the gas escape openings is adapted for being blocked. The microfluidic device may e.g. comprise a first and a second gas escape opening, the first escape opening being arranged downstream to the flow controlling section and the second escape opening being arranged downstream to the liquid flow channel section and upstream to the flow controlling section, the second escape opening being blocked during a part of the use of the microfluidic device. In use the second escape opening is initially blocked. The liquid is loaded into the liquid flow channel. The liquid will flow into the liquid flow channel with a velocity controlled by the flow controlling section. At a certain stage the second escape opening is deblocked for allowing a free escape of gas, whereby the flow controlling section will be set out of function, and a liquid flow which is no longer limited by gas resistance effects will occur.

In one embodiment the microfluidic device may e.g. comprise a first and a second gas escape opening, the first escape opening is placed between the inlet and a liquid flow channel section and is an ordinary escape opening, where the flow resistance provided by an out flowing gas is insignificant compared to the flow resistance provided by a liquid in the liquid flow channel section channel. A preliminary liquid flow channel section and/or one or more chambers (mixing chambers and/or reaction chambers) is/are arranged between the inlet and the first gas escape. Downstream to the first escape opening may be an additional liquid flow channel section and downstream to the preliminary liquid flow section and/or the additional liquid flow channel section is a flow controlling section upstream to or coinciding with the second escape opening. In use, the liquid is loaded into the inlet, and quickly floods at least a part of the preliminary liquid flow channel section and/or one or more chambers while the gas driven away by the liquid flows out via the first escape opening without thereby resulting in any significant resistance liquid flow channel. The first escape opening is thereafter blocked, e.g. by a tape or by a fluid (e.g. the fluid in the preliminary liquid flow channel section) so that the only way the gas can escape is via the second gas escape, and consequently the gas has to pass through the flow controlling section. The liquid will continue its flow in the preliminary liquid flow channel section and/or in the additional liquid flow channel section while the gas driven away by the liquid passes through the flow controlling section and out of the second gas escape opening.

The skilled person will be able to modify the above embodiments within the scope of this invention to provide microfluidic devices with two or more optionally blockable gas escape openings.

In one embodiment the microfluidic device comprises at least one gas escape openings which is adapted for being blocked by covering the gas escape with a gas tight element, such as tape and or a plug.

In one embodiment where the microfluidic device comprises two or more gas escape openings, at least one of the gas escape openings is adapted for being blocked by liquid in the liquid flow channel section.

In one embodiment the microfluidic device comprises a flow channel with an inlet and a gas escape opening, the flow channel comprises a liquid flow channel section and a flow controlling section downstream to the liquid flow channel section and coinciding with the gas escape opening, and wherein the flow controlling section provides a flow resistance to gas, which is sufficiently high to reduce velocity of a capillary flow of a liquid in the liquid flow channel section. In this embodiment the flow controlling section may e.g. be provided with one or more narrow passages as described above.

In one embodiment wherein the gas escape opening is sufficiently small to provide a flow resistance to gas, the gas escape opening provides a flow resistance against gas which is sufficiently high to be the controlling factor of the velocity of a liquid fluid flow in the liquid flow channel. The gas escape opening may for example comprise a gas resistance unit e.g. in the form of gas permeable tape as described above.

The invention also relates to a method of performing a test of a liquid sample wherein the method comprises

- providing a microfluidic device as described above
- applying the sample to the flow channel via the inlet;
- allowing the sample to flow in the liquid flow channel section; and
- determining at least one parameter.

The method of the invention has shown to provide increasingly accurate measurements and even allows the possibility of performing measurements which heretofore have not been possible due to lack of sufficient control of the flow in the micro-channel of a microfluidic device.

In particular when the test involves chemical reactions in the microfluidic device, the method of the invention has shown to be very beneficial and to be able to provide highly reliable results. In particular it is desired that the sample is allowed to flow in the liquid flow channel section at a velocity which is lower than it would have been without the flow controlling section.

In principle the liquid sample can be any kind of liquid sample, biological or not biological.

In one embodiment the sample may comprise antibodies, antigens, polypeptides, enzymes, nucleic acids, such double stranded, partly single stranded and single stranded DNA, RNA, LNA and/or PNA In one embodiment the sample may comprise a biological fluid such as blood, urine, saliva, sperm and/or one or more fractions thereof.

In one embodiment the sample may comprise microorganism, yeast, fractions thereof and/or components produced there from.

The method has shown to be extremely useful for performing coagulation tests and/or agglutination tests. The reason for this is believed to be that the high control of the flow provided by the method provides an optimal environment for allowing the coagulation and/or agglutination to occur while simultaneously keeping the flow at a level where the parameter determined can be made with a high accuracy.

For performing the test the sample is contacted with at least one reagent prior to applying it to the flow channel and/or the sample is contacted with a reagent in the microfluidic device such as it is well known in the art. The reagents used for performing such reactions are also well known and may for example comprise coagulation promoting reagent, such as thromboplastin, chemical lysing agents and/or an agglutination reagent, such as Anti citrate and an agglutination reagent, such as Anti-A antisera, Anti-B antisera and latex microspheres with attached antibodies.

The at least one parameter may be determined by any method. In one embodiment the parameter determined is determined at least partly by visual inspection, optical inspection and/or electrical read out. Visual inspection as well as optical inspection will in most situations require that at least a part of the microfluidic device is transparent to such a degree that the liquid flow in the liquid flow section can be followed visually by optical means. Methods for performing optical measurements are well known and need no further description for the skilled person. As examples it can be mentioned that optical measurements may be performed by fluorescence polarization detectors, fluorescence fluctuation detectors, particle counting sensors, concentration detection sensors, light absorption sensors, and light scattering sensors.

Examples of optical polarization detectors are for example disclosed in WO 99/64840. Examples of concentration detection sensors are for example disclosed in U.S. Pat. No. 5,569,608. Examples of particle counting sensors are for example disclosed in US 2004/0011975 and WO 2004/042402 (using scattered light).

Examples of quantification units include laser induced fluorescence detectors, such as laser detectors with a light emission capable of excitating a marker and comprising a photo sensor such as a photo-multiplier tube (PMT), an avalanche photodiode (ADP) or a charge coupled device (CCD).

Examples of laser induced fluorescence detectors are for example disclosed in US 2005/020666 and WO 2006/098752.

Electrical read out may for example be performed by simple electrical circuits which are activated due to an electrical contact provided by the liquid sample in the flow channels and/or by piezoresistive or pizoelectrical sensors.

In one embodiment the at least one parameter preferably comprises at least a change in flow rate, a change in viscosity, a change in agglutination time and/or a change in agglutination degree.

According to the method of the invention it has been found that in particular agglutination tests are sensitive to lack of control of flow as in prior art methods. Heretofore it has been very difficult or even impossible to perform agglutination tests in microfluidic devices with a reliable result.

By using the method of the invention for performing agglutination tests highly improved or even new tests have been provided.

It is believed that the success of the present method for performing an agglutination test is a result of the control of the flow rate in the microfluidic device, which makes it possible to adjust the velocity and/or the shear stress such that damaging of formed clots and/or aggregates can be highly reduced or even avoided.

In one embodiment the test is an agglutination test and the velocity of the flow front of the sample in the liquid flow channel section is adjusted to be sufficiently slow to avoid damaging formed clots and/or aggregates.

The velocity of the flow front may preferably be at least about 0.01 mm/s in order to make the agglutination occur. If the flow is completely stopped the agglutination process will be very slow or it may even stop as well. A minimum flow of about 0.01 mm has been found to be workable.

In one embodiment the test is an agglutination test and the velocity of the flow front of the sample in the liquid flow channel section is in the interval from about 0.01 to about 20 mm/s, such as from about 0.05 to about 5 mm/s, such as from about 0.1 to about 1 mm/s, until the determination of the at least one parameter has been performed and/or until the agglutination has substantially been terminated.

The shear stress also has an influence on potentially damaging formed clots and/or aggregates. The shear stress is in most situations proportional to the liquid flow, however when the liquid in a non-Newtonian liquid or the flow channel section is not straight and without changes along its length, it may be desired to keep the shear stress under a certain level to avoid damaging formed clots and/or aggregates.

If the shear stress should be lowered this may simply be done by reducing the velocity of the flow. Alternatively the surface characteristics of the channels can be modified (e.g. smoother surfaces may be provided), the geometry of the channels may be modified, the temperature and thereby the viscosity may be chained and etc. For providing a sufficiently low share rate the flow controlling section of the microfluidic device used in the method of the invention has shown to an essential element optionally in combination with any of the above indicated methods of lowering shear stress.

The shear stress may for example be determined using micro particle image velocimetry (Micro-PIV).

Accordingly in one embodiment the shear stress is about 150 $s^{-1}$ or less.

In one embodiment the velocity of the sample in the liquid flow channel section provides a shear stress which is in the interval from about 0.01 to about 150 $s^{-1}$, such as from about 0.1 to about 50 such such as from about 1 to about 10 $s^{-1}$, until the determination of the at least one parameter has been performed and/or until the agglutination has been substantially terminated.

BRIEF DESCRIPTION OF DRAWINGS

Examples of embodiments of the invention will be described below with references to the drawings.

The figures are schematic and simplified for clarity, and they just show details which are essential to the understanding of the invention, while other details are left out. Throughout, the same reference numerals are used for identical or corresponding parts.

In the figures shown the top side of the respective microfluidic devices is of transparent material so that the flow channels can be seen. It should be understood that the topside and/or the bottom side of the microfluidic device of the invention need not be transparent but may be partly or totally non-transparent if desired. For example in one embodiment only the inlet and the liquid flow channel section or a part thereof are visible, whereas in another embodiment only the inlet is visible and in yet other embodiments also the gas escape opening is visible.

Figure 1:
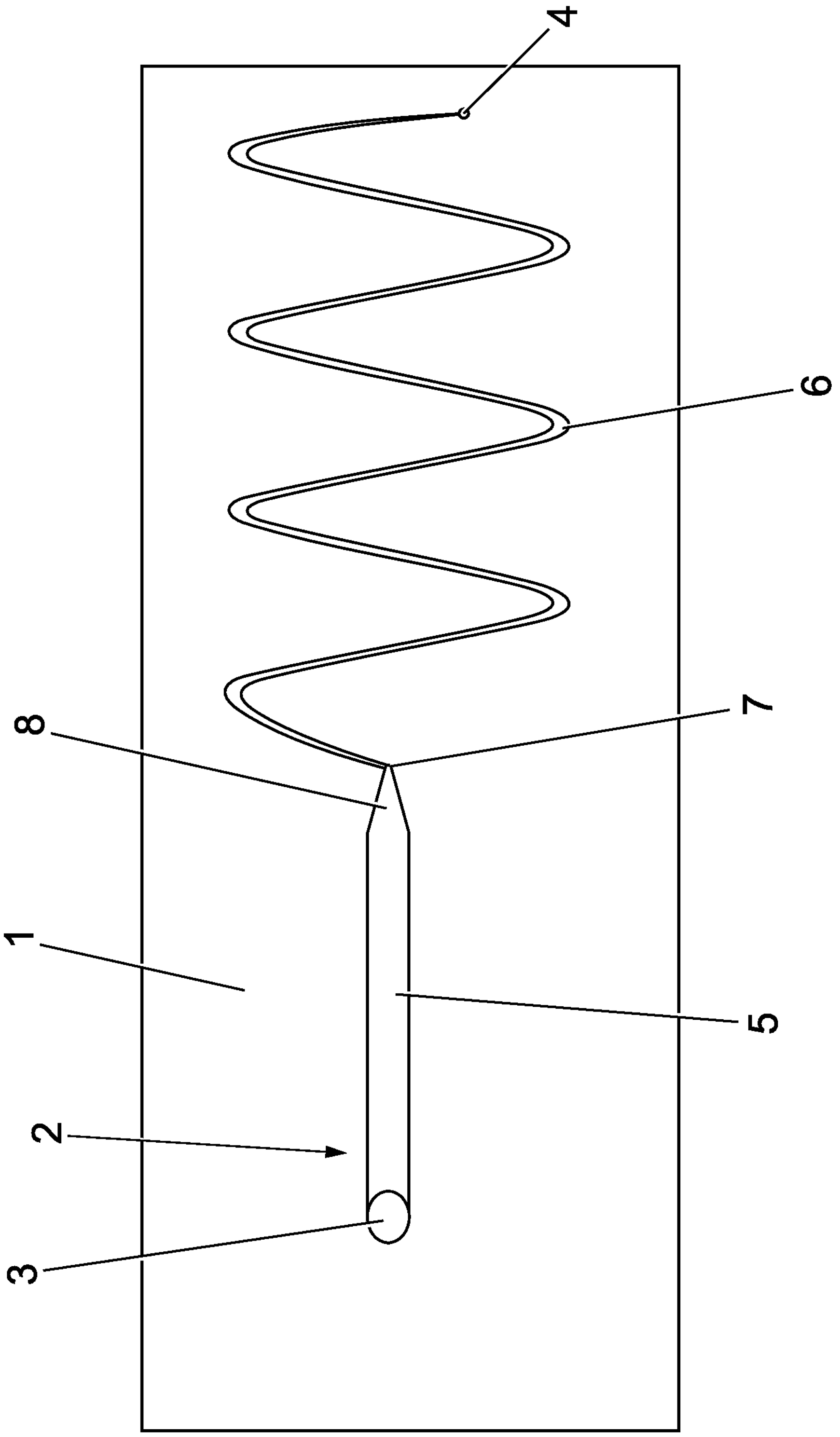
FIG. 1 shows a top view of a first microfluidic device of the invention.

FIG. 1 is a top view of a first microfluidic device of the invention. The microfluidic device is formed as a slide 1 e.g. of glass or polymer comprising a flow channel 2. The flow channel 2 comprises an inlet 3, a gas escape opening 4, a liquid flow channel section 5 and a flow controlling section 6 downstream to the liquid flow channel section 5 and upstream to the gas escape opening 4. The flow controlling section provides a flow resistance to gas, which is sufficiently high to reduce velocity of a capillary flow of a liquid in the liquid flow channel section. The flow controlling section 6 comprises a flow controlling section entrance 7 where the channel becomes sufficiently small to provide a resistance to the gas when a liquid sample is applied to the inlet 3 and passes into the liquid flow channel section 5. In the embodiment shown in FIG. 1 the transition 8 of the liquid flow channel section 5 to the flow controlling section entrance 7 is gradual. In other embodiments it may be abrupt. The flow controlling section 6 is meander shaped and the cross sectional area of the flow controlling section 6 along its length varies as shown. The cross sectional area of the flow controlling section 6 may be much smaller compared to the cross sectional area of the liquid flow channel section than indicated on the figure, where only the width of the respective channels can be seen. The cross sectional area may preferably be as described above. Also the flow controlling section 6 may be longer than indicated in the figure.

Figure 2:
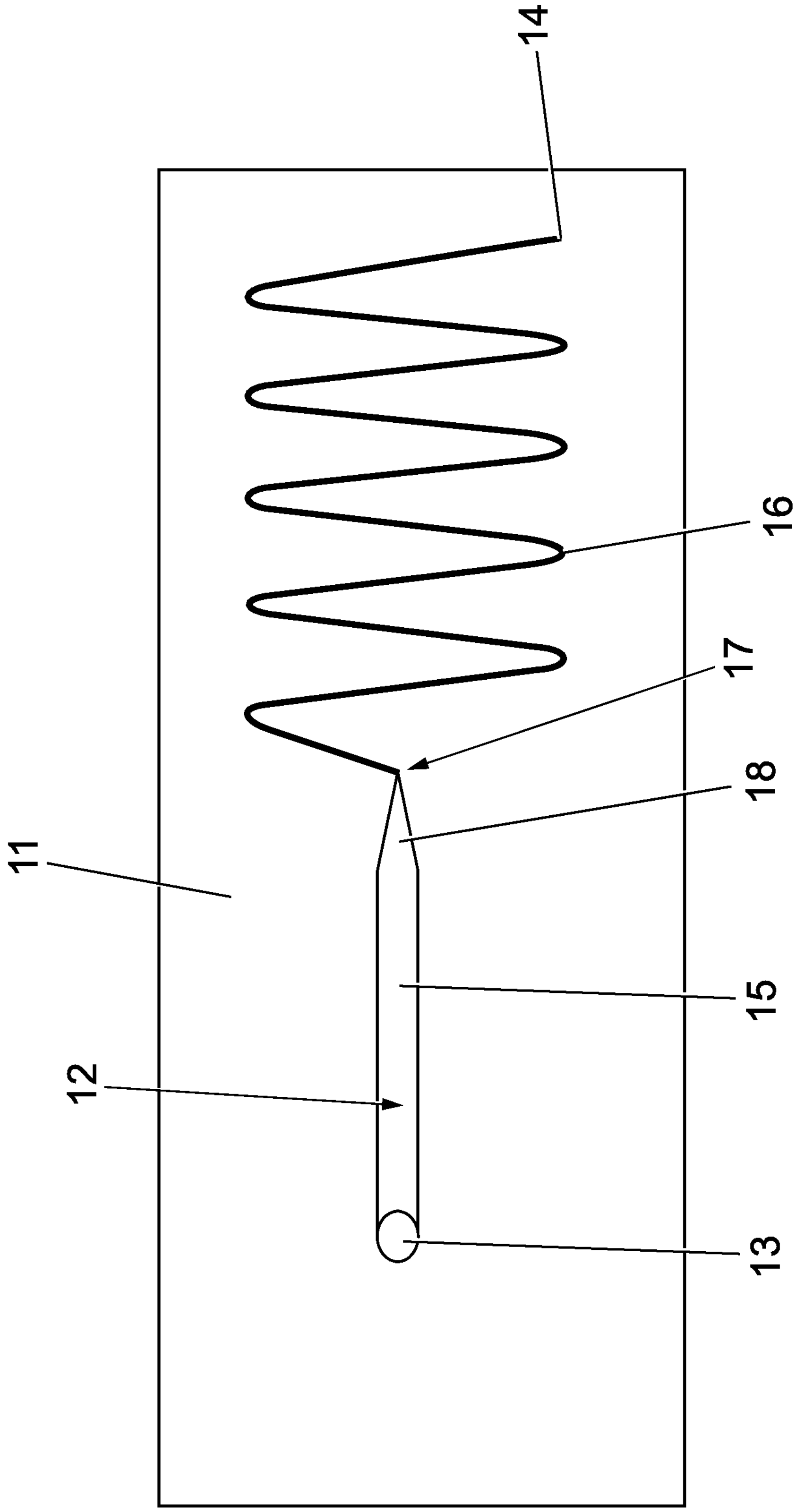
FIG. 2 shows a top view of a second microfluidic device of the invention.

FIG. 2 is a top view of a second microfluidic device of the invention. Also here the microfluidic device is formed as a slide 11. It should be understood that the microfluidic device could have other shapes, for example it could have an oval or round outer periphery and or it could be relatively thick and e.g. comprising two or more layers of flow channels. The microfluidic device in FIG. 2 comprises a flow channel 12 comprising an inlet 13, a gas escape opening 14, a liquid flow channel section 15 and a flow controlling section 16 downstream to the liquid flow channel section 15 and upstream to the gas escape opening 14. The flow controlling section provides a flow resistance to gas, which is sufficiently high to reduce velocity of a capillary flow of a liquid in the liquid flow channel section. The flow controlling section 16 comprises a flow controlling section entrance 17 where the channel becomes sufficiently small to provide a resistance to the gas when a liquid sample is applied to the inlet 13 and passes into the liquid flow channel section 15. The liquid flow channel section 15 comprises a tapered transition 18 to the flow controlling section entrance 17. The flow controlling section 16 is meander shaped and the cross sectional area of the flow controlling section 16 along its length is essentially constant.

Figure 3:
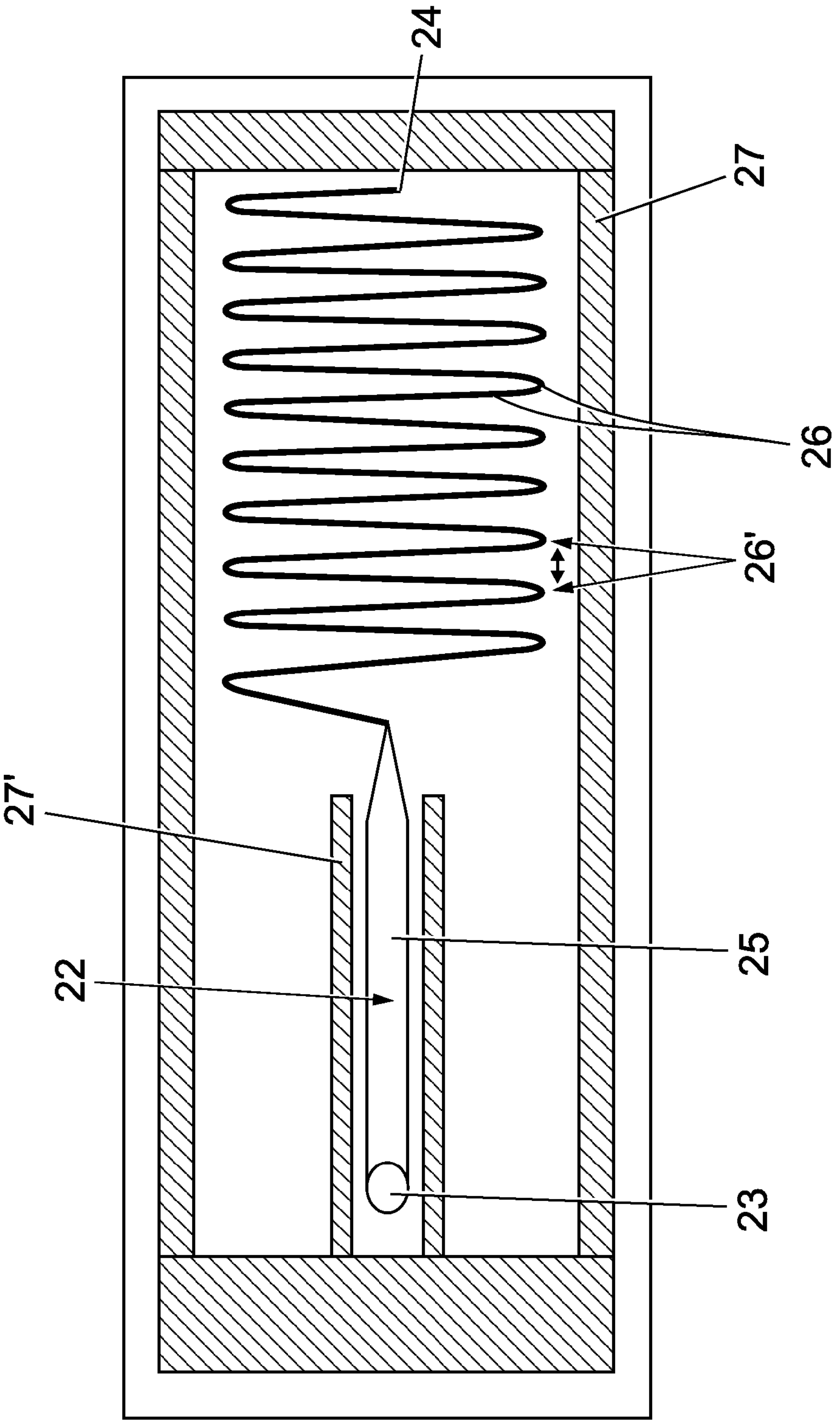
FIG. 3 shows a top view of a third microfluidic device of the invention.

FIG. 3 is a top view of a third microfluidic device of the invention which is a variation of the microfluidic device shown in FIG. 2. The microfluidic device comprises a flow channel 22 comprising an inlet 23, a gas escape opening 24, a liquid flow channel section 25 and a flow controlling section 16 downstream to the liquid flow channel section 25 and upstream to the gas escape opening 24. The flow controlling section provides a flow resistance to gas, which is sufficiently high to reduce velocity of a capillary flow of a liquid in the liquid flow channel section. The flow controlling section 26 comprises a flow controlling section entrance 27 where the channel becomes sufficiently small to provide a resistance to the gas when a liquid sample is applied to the inlet 23 and passes into the liquid flow channel section 25. The flow controlling section 26 is meander shaped with windings which are closer to each other than in the microfluidic device shown in FIG. 2. In order to provide a relatively compact microfluidic device it is in general desired to fold the flow controlling section as much as possible thereby making the flow controlling section as long as possible within the smallest place possible, However, care should be taken that the air flowing within the flow controlling section under relatively high pressure to overcome the flow resistance does not find alternative routes. In many situations the microfluidic device is provided by joining a top and a bottom part together wherein the desired pattern/patterns for the flow channel(s) are provided in one or both of the top and bottom parts. The joining may e.g. be performed by welding. In order to ensure that the flow channel(s) is not blocked during the welding the welding line may be kept at a distance from the flow channel and along the flow channel. However, if the folds 26' of the flow controlling section are very compact it may be difficult to weld along the flow controlling section and maintain the desired distance to avoid blocking the flow controlling section. In the embodiment in FIG. 3 the welding lines 27, 27' are indicated. As it can be seen, welding lines 27' are provided along the liquid flow channel section 25, whereas welding lines are not provided along the whole length of the flow controlling section 26, but only along the folds of the flow controlling section 26. The top and bottom parts are pressed together to provide a tight contact. However, if the pressure within the flow controlling section 26 becomes too high and if the distance between the folds 26' is too short, the air may find alternative flowing paths and for example flow across from one fold 26' of the flow controlling section to another fold 26' of the flow controlling section without following the whole length of the flow controlling section. In principle, if the flow controlling section 26 is sufficiently long, the flow resistance provided by the flow controlling section 26 will still be sufficient even if a few parts of the flow controlling section 26 are bypassed due to the formation of alternative and shorter flowing path for the gas. However, if too many alternatively flowing paths are formed, the flow controlling section 26 may not provide the desired flow resistance. By increasing the distance between the folds 26', the risk of formation of alternative and shorter flowing paths for the gas can be reduced.

Figure 4:
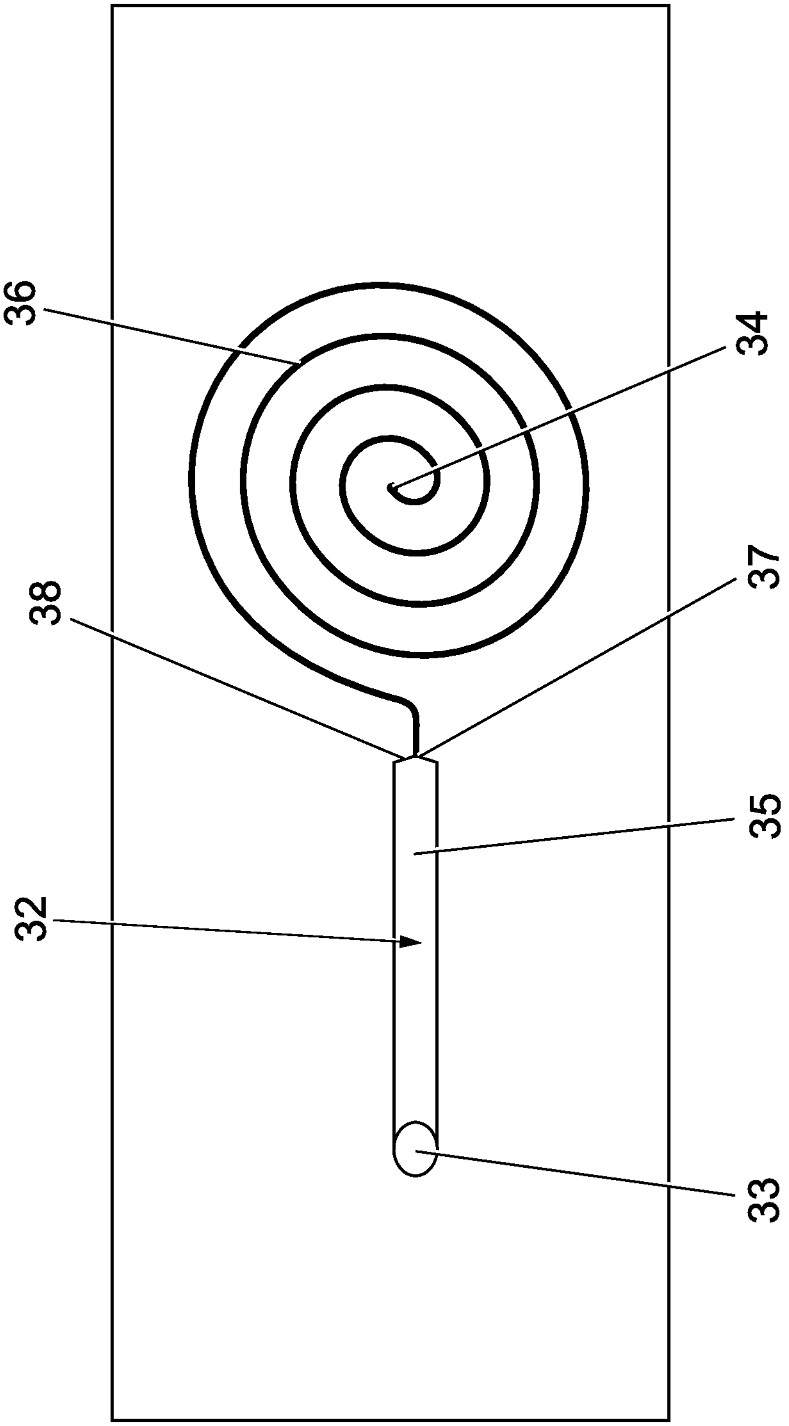
FIG. 4 shows a top view of a fourth microfluidic device of the invention.

FIG. 4 is a top view of a fourth microfluidic device of the invention The microfluidic device comprises a flow channel 32 comprising an inlet 33, a gas escape opening 34, a liquid flow channel section 35 and a flow controlling section 36 downstream to the liquid flow channel section 35 and upstream to the gas escape opening 34. The flow controlling section provides a flow resistance to gas, which is sufficiently high to reduce velocity of a capillary flow of a liquid in the liquid flow channel section. The flow controlling section 36 comprises a flow controlling section entrance 37 where the channel becomes sufficiently small to provide resistance to the gas when a liquid sample is applied to the inlet 33 and passes into the liquid flow channel section 35. The liquid flow channel section 35 comprises a tapered transition 18 to the flow controlling section entrance 37. The flow controlling section 36 is shaped as a coil with a number of windings. The number of windings and the optimal distance of the windings can be found by the skilled person using the teaching above.

Figure 5:
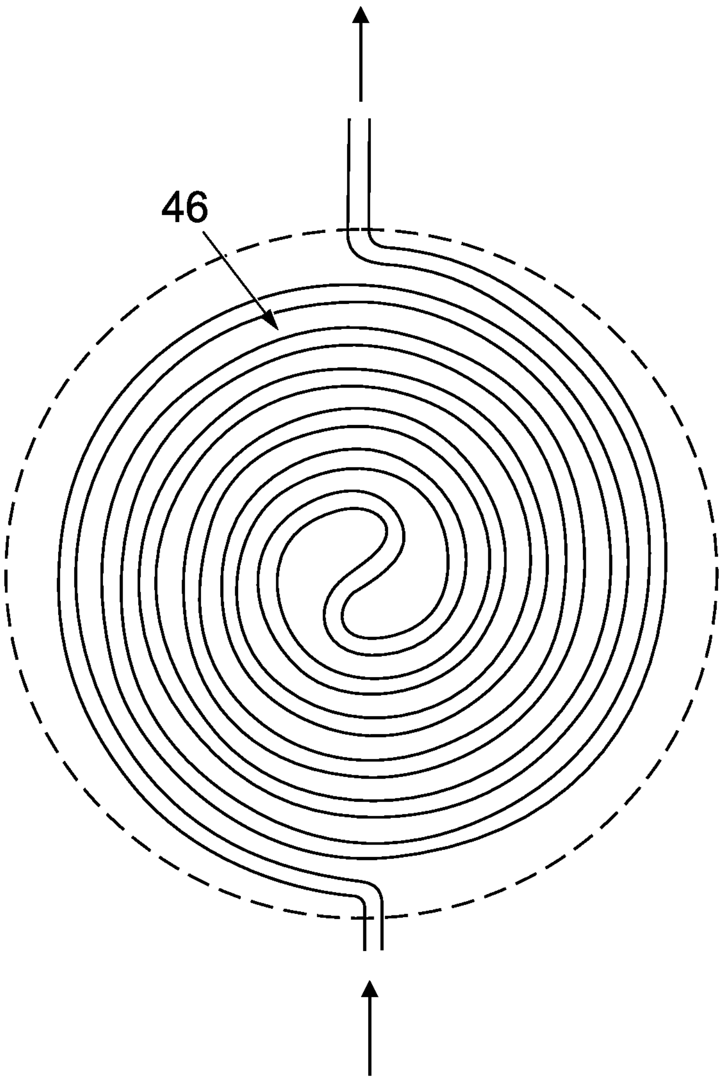
FIG. 5 shows a top view of a flow controlling section of a fifth microfluidic device.

FIG. 5 shows a top view of a flow controlling section 46 of a fifth microfluidic device. Here the flow controlling section is shaped as a double coil. The arrow shows the flow direction of the gas. The double coil shape provide a very compact arrangement of the flow controlling section and a very long length of flow controlling section can be arranged on relatively small area. However, due to the compact arrangement of the flow controlling section, there may also be a risk that the escaping gas will short circuit and find a shorter way, in particular if the pressure drop over the flow controlling section is relatively high. The flow controlling section may e.g. be provided by incorporating a hollow fiber in the microfluidic device. Such hollow fiber can be folded to a very compact unit without the risk of the passing gas short circuiting.

Figure 6:
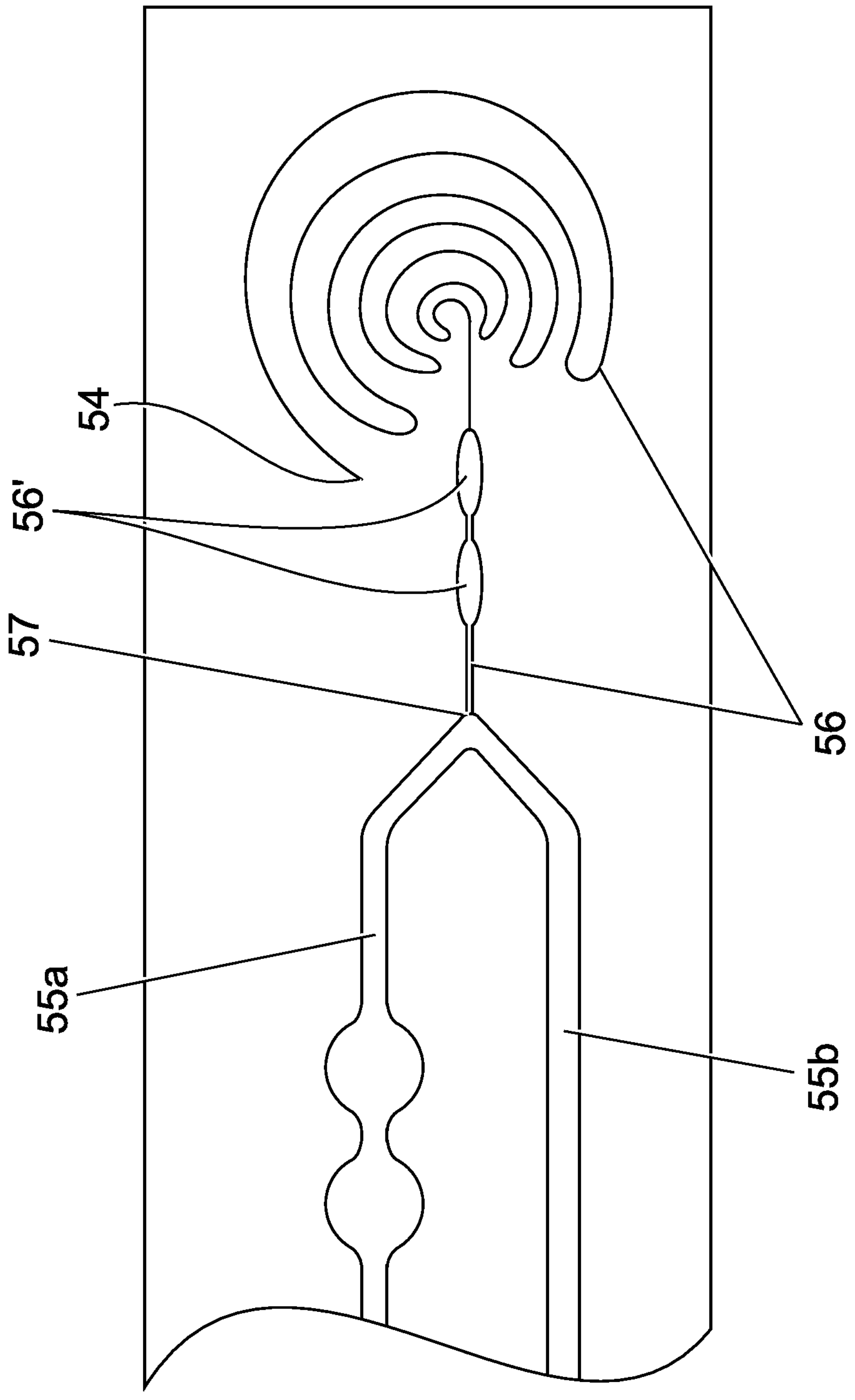
FIG. 6 shows a top view of a part of a sixth microfluidic device of the invention.

FIG. 6 shows a top view of a part of a sixth microfluidic device of the invention. The microfluidic device comprises two liquid flow channel sections 55*a*, 55*b*. The two liquid flow channel sections 55*a*, 55*b* may be distinct liquid flow channel sections and comprising separate not shown inlets or they may have a common not shown inlet and only be separated for a part of their lengths. The two liquid flow channel sections 55*a*, 55*b* may be equal or they may differ from each other e.g. with respect to one or more of length cross sectional areas, presence of one or more chambers, e.g. reaction chambers, inner surface characteristics and other. In the shown embodiment one of the liquid flow channel sections 55*a* comprises two chambers, e.g. reaction chambers whereas the other one of the liquid flow channel sections 55*b* does not comprise any reaction chambers. The two liquid flow channel sections 55*a*, 55*b* comprise a common flow controlling section 56. The flow controlling section comprises two chamber like parts 56' having high cross-section compared to the cross section of the remaining part of the flow controlling section (low cross section part(s). It should be understood that the number and length of high cross sections parts may vary from embodiment to embodiment. At part of the flow controlling section 56 is folded in double C shapes. The flow controlling section terminates in a gas escape 54. The flow controlling section 56 provides a flow resistance to gas, which is sufficiently high to reduce velocity of a capillary flow of a liquid in at least one of the liquid flow channel sections 55*a*, 55*b*. The flow controlling section 56 comprises a flow controlling section entrance 57 where the channel becomes sufficiently small to provide resistance to the flow of gas. The transition from liquid flow channel sections 55*a*, 55*b* to the flow controlling section entrance 57 is abrupt. This abrupt transition or if desired a liquid flow stop, such as a hydrophobic liquid flow stop or a geometric liquid flow stop may be arranged prior to providing a barrier for liquid to flow into the flow controlling section if one or both of the liquid flow channel sections 55*a*, 55*b* should be filled with liquid.

Figure 7:
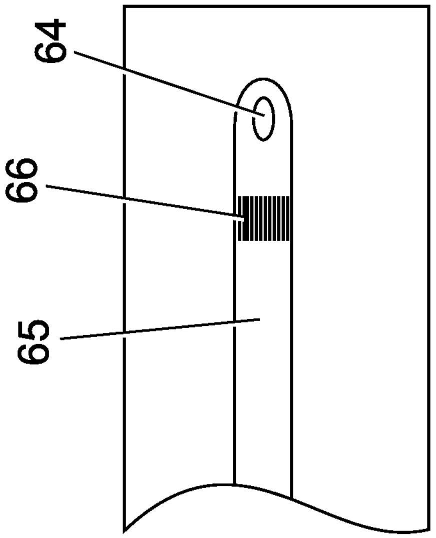
FIG. 7 shows a top view of a part of a seventh microfluidic device of the invention.

FIG. 7 shows a top view of a part of a seventh microfluidic device of the invention. The microfluidic device comprises a liquid flow channel section 65, a not shown inlet, a gas escape opening 64, and a flow controlling section 66 downstream to the liquid flow channel section 65 and upstream to the gas escape opening 64. The flow controlling section 66 provides a flow resistance to gas, which is sufficiently high to reduce velocity of a capillary flow of a liquid in the liquid flow channel section 65. The flow controlling section 66 is provided by a plurality of narrow passages in the flow channel provided by a gas permeable membrane or plug placed in the flow channel. The membrane may e.g. be a PTFE membrane. The plug may e.g. be a porous polymer, a compacted fiber material or other material providing the desired gas permeability/resistance.

Figure 8:
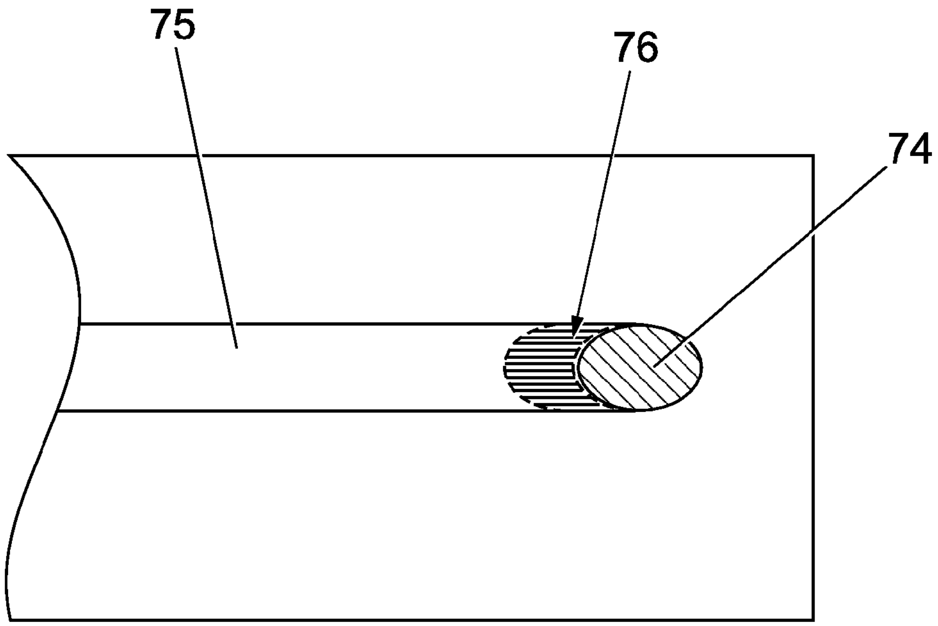
FIG. 8 shows a top view of a part of an eighth microfluidic device of the invention.

FIG. 8 shows a top view of a part of an eighth microfluidic device of the invention. The microfluidic device comprises a liquid flow channel section 75, a not shown inlet, a gas escape opening 74, and a flow controlling section 76 downstream to the liquid flow channel section 75 and coinciding with the gas escape opening 74. The flow controlling section 76 provides a flow resistance to gas, which is sufficiently high to reduce velocity of a capillary flow of a liquid in the liquid flow channel section 75. The flow controlling section 76 is provided by a plurality of narrow passages in the flow channel provided by a gas permeable membrane or plug placed in the flow channel. The membrane may e.g. be a PTFE membrane. The plug may e.g. be a porous polymer, a compacted fiber material or other material providing the desired gas permeability/resistance.

Figure 9:
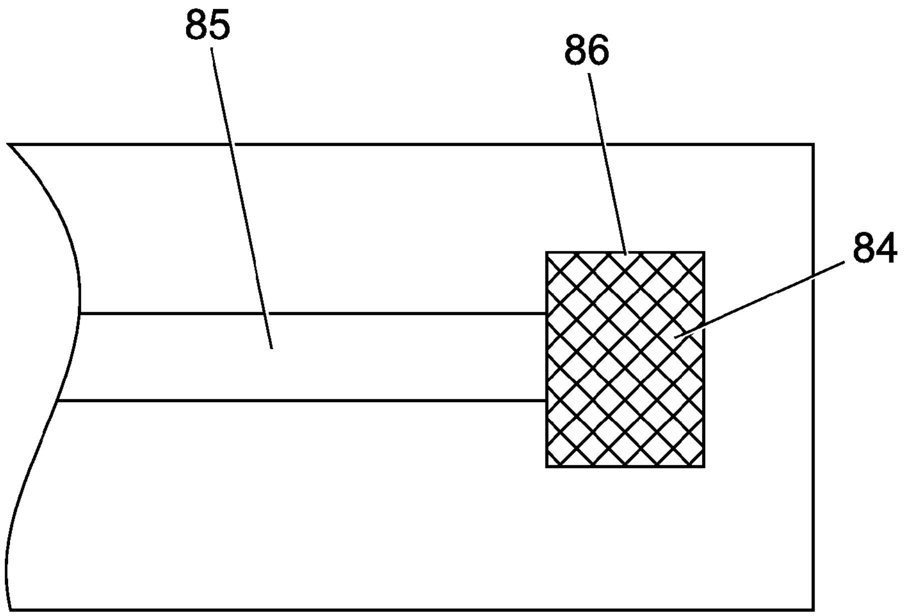
FIG. 9 shows a top view of a part of a ninth microfluidic device of the invention.

FIG. 9 shows a top view of a part of a ninth microfluidic device of the invention. The microfluidic device comprises a liquid flow channel section 85 a not shown inlet, a gas escape opening 84, and a flow controlling section 86 downstream to the liquid flow channel section 85 and coinciding with the gas escape opening 84. The flow controlling section 86 provides a flow resistance to gas, which is sufficiently high to reduce velocity of a capillary flow of a liquid in the liquid flow channel section 85. The flow controlling section 86 is provided either by a plurality of narrow passages in the flow channel provided by a gas permeable membrane e.g. a PTFE membrane or a single small hole in a film covering the gas escape opening 84. The hole or the passages should be sufficiently narrow to provide the desired gas resistance.

Figure 10:
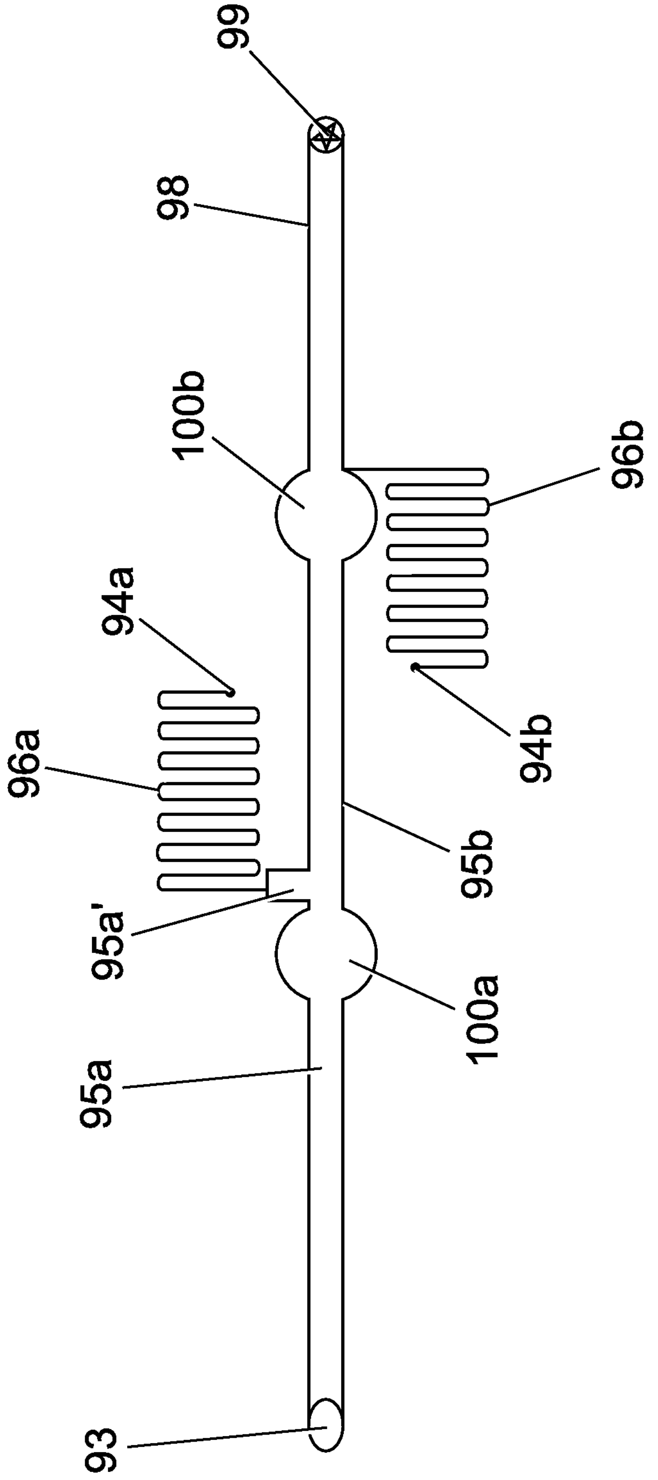
FIG. 10 shows a top view of a tenth microfluidic device of the invention.

FIG. 10 shows a top view of a tenth microfluidic device of the invention. The microfluidic device comprises a liquid flow channel section 95*a*, 95*b*, with a first liquid flow channel section part 95*a* and a second liquid flow channel section part 95*b*, an inlet 93, a first and a second gas escape opening 94*a*, 94*b*, and a first and a second meander folded flow controlling section 96*a*, 96*b* downstream to respectively the first and the second liquid flow channel sections 95*a*, 95*b* and upstream to respectively the first and the second gas escape openings 94*a*, 94*b*. The first liquid flow channel section part 95*a* comprises a chamber 100*a* for example for allowing a liquid to react with and/or dissolve/disperse a component applied in the chamber 100*a*. The first liquid flow channel section part 95*a* comprises a branch 95*a'* terminating with a narrowing (here an abrupt narrowing) to an entrance to the first flow controlling section 96*a*. The branch 95*a'* and/or the first flow controlling section 96*a* may e.g. be provided with a liquid flow stop for preventing liquid to flow into and/or to pass through the first flow controlling section 96*a*. The second liquid flow channel section part 95*b* is arranged distal to the branch 95*a*'. In this embodiment also the second liquid flow channel section part 95*b* comprises a chamber 100*b*, and immediately downstream to the chamber 100*b*, it comprises the second flow controlling section 96*b*. Also the second flow controlling section may comprise a liquid flow stop. Downstream to the second liquid flow channel section part 95*b* is arranged a terminal liquid flow channel section 98 with a terminating cover 99, which may for example be perforated with a needle if desired.

In use the second escape opening 94*b* may initially be closed with a tape. A liquid is fed to the inlet 93 and flows into the first liquid flow channel section part 95*a* and fills up the chamber 100*a*. The gas driven away by the liquid has to flow through the first flow controlling section 96*a* and out of the first escape opening 94*a*. The velocity of the flow is thereby controlled by the flow resistance to gas in the first flow controlling section 96*a*. When the liquid has reached and filled the branch 95*a*', the liquid flow stops. Due to the liquid flow stop of the branch 95*a*', liquid will not flow into the first flow controlling section 96*a*.

When the second escape opening 94*b* is opened e.g. by removing the tape, the liquid flow will continue to flow into the second liquid flow channel section part 95*b* and to fill up the chamber 100*b*. The gas driven away by the liquid has to flow through the second flow controlling section 96*b* and out of the first escape opening 94*b*. The velocity of the flow is thereby controlled by the flow resistance to gas in the second flow controlling section 96*b*. When the liquid has reached the entrance to the second flow controlling section 96*b*, the liquid flow will again stop. Due to the liquid flow stop in the second flow controlling section 96*b*, liquid will not flow into the second flow controlling section 96*b*. By perforating the terminating cover 99 the liquid will flow further into the terminal liquid flow channel section 98.

In another embodiment which is an alternative to the embodiment of FIG. 10 the first gas escape opening is an ordinary gas escape opening which does not provide any significant resistance to passing gas, and it is arranged directly on the branch 95*a*' without the first flow controlling section 96*a*. The branch 95*a*' is provided with a liquid flow stop for preventing liquid to fill the branch 95*a*', and or to pass out of the first escape opening.

In use the second escape opening 94*b* need not be closed. A liquid is fed to the inlet 93 and will quickly flood at least a part of the first liquid flow channel section part 95*a* and the chamber 100*a*. The gas driven away by the liquid passes out of the first escape opening without providing any significant resistance. The velocity of the flow is thereby controlled by the flow resistance to the liquid in the first flow controlling section 96*a*. When the liquid has reached the branch 95*a*' the liquid flow slows down and the flow controlling effect of the second flow controlling section 96*b* kicks in and controls the velocity of the further flow of the liquid. Due to the liquid flow stop of the branch 95*a*', liquid will not flow into the first flow controlling section 96*a*, but the branch 95*a*' will be blocked so that gas cannot longer escape via the first escape opening. The continued flow is as described above for FIG. 10.

Figure 11:
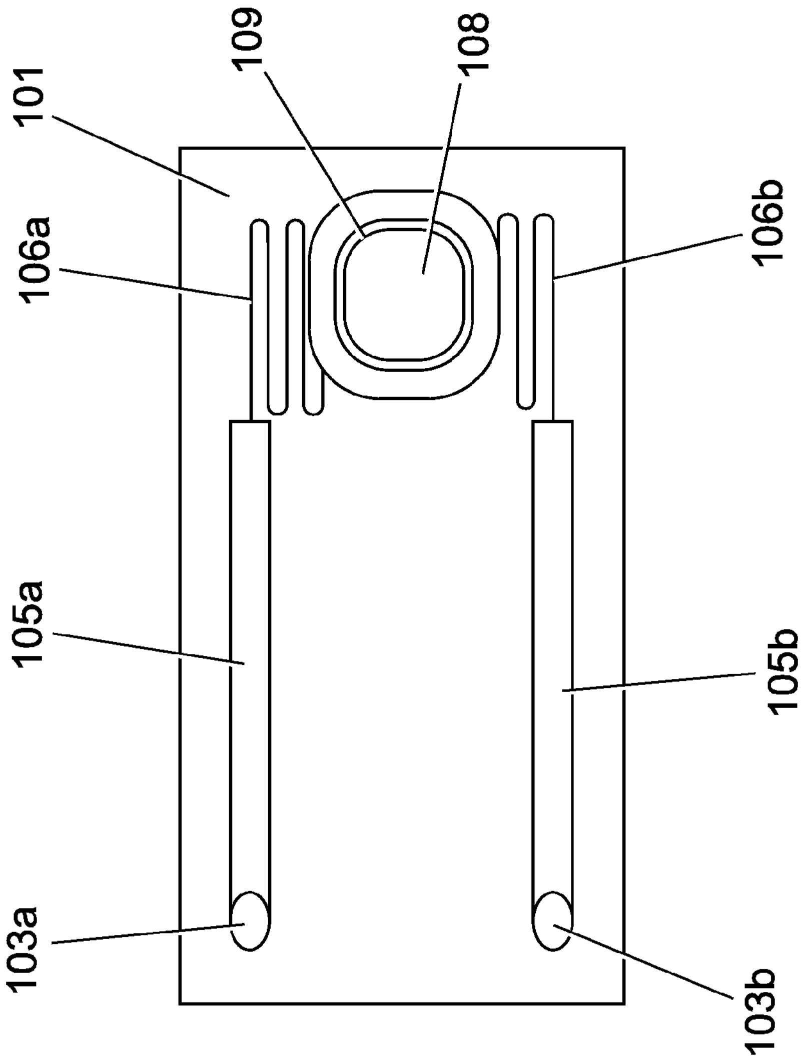
FIG. 11 shows a top view of an eleventh microfluidic device of the invention.

FIG. 11 shows a top view of an eleventh microfluidic device of the invention. The microfluidic device is formed as a slide 101 and comprises two liquid flow channel sections 105*a*, 105*b*. The two liquid flow channel sections 105*a*, 105*b* comprise each an inlet 103*a*, 103*b*. Downstream to each of the two liquid flow channel sections 105*a*, 105*b* is arranged a meander folded flow controlling section 106*a*, 106*b* terminating in a common or in individual not shown gas escape openings. The one or more gas escape openings is/are covered by an inflatable cover 108 which is fixed to the device along a fixing line 109 e.g. by welding.

In use liquid is fed to each of the inlets 103*a*, 103*b* and the liquid flows into the respective liquid flow channel sections 95*a*, 95*b*. The gas driven away by the liquid has to flow through the respective flow controlling sections 96*a*, 96*b*, out of an escape opening and into the space provided by the inflatable cover 108. The velocity of the flow is thereby controlled by the flow resistance to gas in the respective flow controlling section 96*a*, 96*b*.

The skilled person will understand that the various details described above and shown in the embodiments in the figures can be modified and combined without departing from the scope of the invention.

The invention claimed is:

1. A microfluidic device comprising a flow channel with an inlet and a gas escape opening, the flow channel comprises a liquid flow channel section and a flow controlling section downstream to the liquid flow channel section and upstream to or coinciding with the gas escape opening, said flow controlling section is in the form of a flow controlling channel section having an average cross sectional area along its length which is at least about 90% smaller than the average cross sectional area of the liquid flow channel, and which flow controlling section provides a flow resistance to gas, which flow resistance is sufficiently high to reduce velocity of a capillary flow of a liquid in the liquid flow channel section.

2. A microfluidic device as claimed in claim 1, wherein said flow controlling section provides a flow resistance to gas, which is sufficiently high to reduce velocity of a capillary flow of a liquid in the liquid flow channel section compared to what the velocity would have been without the flow controlling section.

3. A microfluidic device as claimed in claim 1, wherein said flow controlling section is in the form of at least one narrow passage in the flow channel coinciding with the gas escape opening.

4. A microfluidic device as claimed in claim 1, wherein said flow controlling channel section has a length and a cross section profile along its length arranged to provide a channel flow resistance which is sufficiently high to reduce velocity of a capillary flow of a liquid in the liquid flow channel section.

5. A microfluidic device as claimed in claim 4, wherein the cross section of the flow controlling channel section along its length is essentially constant.

6. A microfluidic device as claimed in claim 4, wherein the cross section of the flow controlling channel section along its length varies.

7. A microfluidic device as claimed in claim 4, wherein the flow controlling channel section has a length of at least about 10 cm.

8. A microfluidic device as claimed in claim 4, wherein the flow controlling channel section has a length which is at least 2 times longer than the liquid flow channel section.

9. A microfluidic device as claimed in claim 4, wherein the cross sectional area in at least a length of the flow controlling channel section is about 10,000 $\mu m^2$ or less.

10. A microfluidic device as claimed in claim 1, wherein the flow controlling section provides a flow resistance which is sufficiently high to reduce velocity of a capillary flow of a liquid in the liquid flow channel section with at least about 10% compared to what the velocity would have been without said flow controlling channel section.

11. A microfluidic device as claimed in claim 1, wherein the flow controlling section provides a flow resistance against gas which is higher than the flow resistance of a liquid fluid flow in the liquid flow channel.

12. A microfluidic device as claimed in claim 11 wherein the flow resistance against gas in the flow controlling section is so high that a liquid flow velocity in the liquid flow channel section is essentially not reduced by liquid flow resistance in said liquid flow channel section.

13. A microfluidic device as claimed in claim 1, wherein the flow controlling channel section is bended, preferably the flow controlling channel is coiled or meander shaped.

14. A microfluidic device as claimed in claim 1, wherein the gas escape opening is an opening into an inflatable unit of the device.

15. A microfluidic device as claimed in claim 1, wherein the gas escape opening is an opening for gas to escape out of the device.

16. A microfluidic device as claimed in claim 1, wherein the flow channel comprises two or more gas escape openings, at least one of the gas escape openings is adapted for being blocked.

17. A microfluidic device as claimed in claim 16 wherein at least one of the gas escape openings is adapted for being blocked by covering the gas escape with a gas tight element, such as tape and or a plug.

18. A microfluidic device as claimed in claim 16 wherein at least one of the gas escape openings is adapted for being blocked by liquid in the liquid flow channel section.

19. A microfluidic device as claimed in claim 16, wherein the device comprises an inlet, a preliminary liquid flow channel section and/or one or more chambers downstream to the inlet, a first escape opening downstream to the preliminary liquid flow channel section and/or one or more chambers, an additional liquid flow channel section downstream to the first escape opening, a flow controlling section downstream to the additional liquid flow channel section and a second escape opening downstream to the flow controlling section, wherein gas can pass out of the first escape opening without any significant resistance, the first escape opening being arranged such that it will be blocked by the liquid when it passes into the additional liquid flow channel section.

* * * * *